United States Patent
Wang et al.

(10) Patent No.: US 10,508,287 B2
(45) Date of Patent: Dec. 17, 2019

(54) METHOD FOR REGENERATING T CELLS AND APPLICATIONS THEREOF

(71) Applicant: Guangzhou Institutes of Biomedicine and Health Chinese Academy of Sciences, Guangzhou (CN)

(72) Inventors: Jinyong Wang, Guangzhou (CN); Dan Yang, Guangzhou (CN); Yong Dong, Guangzhou (CN); Fangxiao Hu, Guangzhou (CN); Qianhao Zhao, Guangzhou (CN); Mengyun Zhang, Guangzhou (CN); Cui Lv, Guangzhou (CN); Ying Wang, Guangzhou (CN)

(73) Assignee: Guangzhou Institutes of Biomedicine and Health Chinese Academy of Sciences, Guangzhou (CN)

( * ) Notice: Subject to any disclaimer, the term of this patent is extended or adjusted under 35 U.S.C. 154(b) by 217 days.

(21) Appl. No.: 15/520,749

(22) PCT Filed: Dec. 28, 2016

(86) PCT No.: PCT/CN2016/112508
§ 371 (c)(1),
(2) Date: Apr. 20, 2017

(87) PCT Pub. No.: WO2018/119715
PCT Pub. Date: Jul. 5, 2018

(65) Prior Publication Data
US 2018/0363007 A1    Dec. 20, 2018

(51) Int. Cl.
*C12N 15/85* (2006.01)
*C12N 15/867* (2006.01)
*C12N 5/0783* (2010.01)
*C12N 5/0781* (2010.01)

(52) U.S. Cl.
CPC ......... *C12N 15/867* (2013.01); *C12N 5/0635* (2013.01); *C12N 5/0637* (2013.01); *C12N 2506/11* (2013.01); *C12N 2510/00* (2013.01); *C12N 2730/00041* (2013.01)

(58) Field of Classification Search
None
See application file for complete search history.

(56) References Cited

U.S. PATENT DOCUMENTS

2016/0032317 A1    2/2016  Rossi et al.

FOREIGN PATENT DOCUMENTS

| CN | 101675341 A | 4/2015 |
|---|---|---|
| EP | 2 970 881 | 1/2017 |

OTHER PUBLICATIONS

Yang et al (Methods Mol. Biol. 2015, vol. 1266, pp. 1-25) (Year: 2015).*
Chen et al., "Hoxb5 marks long-term haematopoietic stem cells revealing a homogenous perivascular niche", Nature, Feb. 11, 2016, pp. 223-227.
Xu et al., "Dynamic Expression of HoxB5 in Lung Tissue of Neonatal Rats with Hyperoxia-Induced Chronic Lung Disease and Its Significance", Journal of Applied Clinical Pediatrics, Feb. 28, 2009, pp. 257-259.

* cited by examiner

*Primary Examiner* — Celine X Qian
(74) *Attorney, Agent, or Firm* — Fay Kaplun & Marcin, LLp

(57) ABSTRACT

The present invention relates to a method for inducing the transdifferentiation of B lymphoid cells into T lymphoid cells using transcription factor Hoxb5, and related products and applications thereof. The method of the present invention specifically comprises: introducing Hoxb5, a nucleic acid molecule encoding Hoxb5 or a construct comprising the nucleic acid molecule into the B lymphoid cells to obtain the B lymphoid cells with overexpressed Hoxb5; then implanting the obtained B lymphoid cells into the body of a subject to obtain regenerated T cell progenitor cells by way of transdifferentiation, and then the T cell progenitor cells differentiate into mature T cells with functions. The regenerated T cells obtained using the method of the present invention are not only functionally normal, but also show no risk of tumorigenesis or extremely low risk of tumorigenesis.

5 Claims, 4 Drawing Sheets

METHOD FOR REGENERATING T CELLS AND APPLICATIONS THEREOF

TECHNICAL FIELD

The present invention relates to the technical field of pharmaceutical bioengineering, and more particularly to a method for inducing the transdifferentiation of B cells into T cells using Hoxb5, related products and applications thereof.

BACKGROUND ART

T cells are indispensable to the immune system. At present, the basic researches have shown that the Pax5 gene deleted murine B cells can be transdifferentiated into T cells. B cells from Ebf1 and Pax5 complex heterozygous mice (Ebf1+/− Pax5+/−) can also be transdifferentiated into T cells. In addition, uncommitted multipotent progenitor cells can be obtained by converting the B progenitor cells via a retro-viral overexpressing approach, and re-differentiate into T cells. However, the generated T cells obtained by the approaches mentioned above are not perfect in functionalities, and even lead to clonal lymphoma. In conclusion, most of the key regulatory genes used by the researchers mentioned above are hematopoietic lineage master regulators, the deletion or overexpression of which would result in functional defects of the regenerated T cells or even tumors. Therefore, de novo lineage switching factors preferentially expressed in hematopoietic stem/progenitor cells, may have the potential to completely change the epigenetic paradigm, and thus achieve T cells by transdifferentiation. Only regenerated T progenitor cells obtained by complete transdifferentiation can follow the developmental process of natural physiologic T lymphocytes, differentiate and mature into functional T cells in vivo, and reduce the risk of tumorigenesis.

SUMMARY

Objective of the Invention

The objective of the present invention is to provide a method for inducing the transdifferentiation of B lymphoid cells into T lymphoid cells using transcription factor Hoxb5, and related products and applications thereof.

The inventor of the present invention has deeply analyzed the transcriptional expression profiles of hematopoietic stem/progenitor cells and mature blood cells of mice by RNA-Seq and bioinformatics techniques, and functionally screened out the candidate transcription factor-Hoxb5; then, he has found through a series of biological experiments that, this transcription factor can not only successfully transdifferentiate the B lymphoid cells into functional T cells, but also avoid the risk of tumorigenesis of the regenerated T cells.

Technical Solution

In order to achieve the above objective, in one aspect, the present invention provides a use of Hoxb5, a nucleic acid molecule encoding Hoxb5 or a construct comprising the nucleic acid molecule in the preparation of (i) a preparation for transdifferentiation of B lymphoid cells into functional T cells, (ii) a medicament for potentiating the immune response, preferably potentiating the immune response associated with T cells and/or (iii) a medicament for prevention or treatment of the immunodeficiency, preferably for prevention or treatment of T cell immunodeficiency.

In the use described above, it is preferable that the B-lymphoid cells are a type of pro-B cells or pre-B cells.

In the second aspect, the present invention provides a type of transformed B lymphoid cells, in which Hoxb5, a nucleic acid molecule encoding Hoxb5 or a construct comprising the nucleic acid molecule is introduced to overexpress Hoxb5, and the B lymphoid cells has a potential to transdifferentiate into T cells.

It is preferable that the B lymphoid cells are a type of either pro-B cells or pre-B cells.

In the third aspect, the present invention provides a use of the transformed B lymphoid cells according to the second aspect in the preparation of (i) a medicament for regeneration of T cells, (ii) a medicament for potentiating the immune response, preferably potentiating the immune response associated with T cells and/or (iii) a medicament for prevention or treatment of the immunodeficiency, preferably for prevention or treatment of T cell immunodeficiency.

In the fourth aspect, the present invention provides a pharmaceutical composition comprising the transformed B lymphoid cells according to the second aspect as an active ingredient, and a pharmaceutically acceptable carrier, an excipient or a diluent.

In the fifth aspect, the present invention provides a method for transdifferentiating B lymphoid cells into functional T cells, comprising:

(1) introducing Hoxb5, a nucleic acid molecule encoding Hoxb5 or a construct comprising the nucleic acid molecule into the B lymphoid cells to obtain the B lymphoid cells with overexpressed Hoxb5;

(2) transplanting the B lymphoid cells obtained in step (1) into the body of a subject to induce transdifferentiation to obtain T cell progenitor cells, which then differentiate into functional T cells.

In the method described above, it is preferable that the B-lymphoid cells are a type of pro-B cells or pre-B cells.

It is preferable that in step (1), the Hoxb5, the nucleic acid molecule encoding Hoxb5 or the construct comprising the nucleic acid molecule carries a tracer, preferably a fluorescent protein tracer, more preferably an EGFP fluorescent protein tracer.

It is preferable that in step (1), the nucleic acid molecule encoding Hoxb5 or the construct comprising the nucleic acid molecule is introduced into the B lymphoid cells by transfection or viral transduction, preferably by retrovirus infection.

In a specific embodiment, the inventor first constructed a Hoxb5 retroviral expression vector, specifically, by designing a restriction enzyme cutting site to recombine the Hoxb5 gene into a reverse transcription expression vector (e.g., pMYs-IRES-EGFP); using a retrovirus packaging system, a high-titer retrovirus containing the Hoxb5 gene was packaged; next, the overexpression of the Hoxb5 gene in mouse pro-/pre-B cells was achieved by virtue of retroviral integration; then, the Pro-/Pre-B cells transducing Hoxb5 were transplanted into a myeloablative recipient mice by retroorbital vein injection; four weeks post-transplantation, the origin and identity of the regenerated T cells were identified by virtue of flow cytometry, PCR, RNA-Seq sequencing and bioinformatics analysis, and the results showed that: the regenerated T cells were indeed derived from the transdifferentiation of Pro-/Pre-B cells; by further combined analysis of the immunophenotypes of the regenerated T cells, their distributions in the lymphatic tissues, TCR receptor rearrangement, and in vitro antibody stimulating proliferation experiment, it was demonstrated that the regenerated T cells function normally; in addition, the risk of tumorigenesis of the regenerated T cells was assessed by continuously monitoring the healthy condition of the transplanted recipient mice, especially the T lymphoid hematopoiesis, and the results showed that: the regenerated T cells obtained by the method of the present invention have no risk of tumorigenesis or extremely low risk of tumorigenesis.

DETAILED DESCRIPTION

For the purpose of understanding the present invention, the following examples are listed below in the present invention. It will be apparent to those skilled in the art that the examples are merely illustrations of the present invention and should not be construed as specific limitations of the present invention.

Example 1

Figure 1:
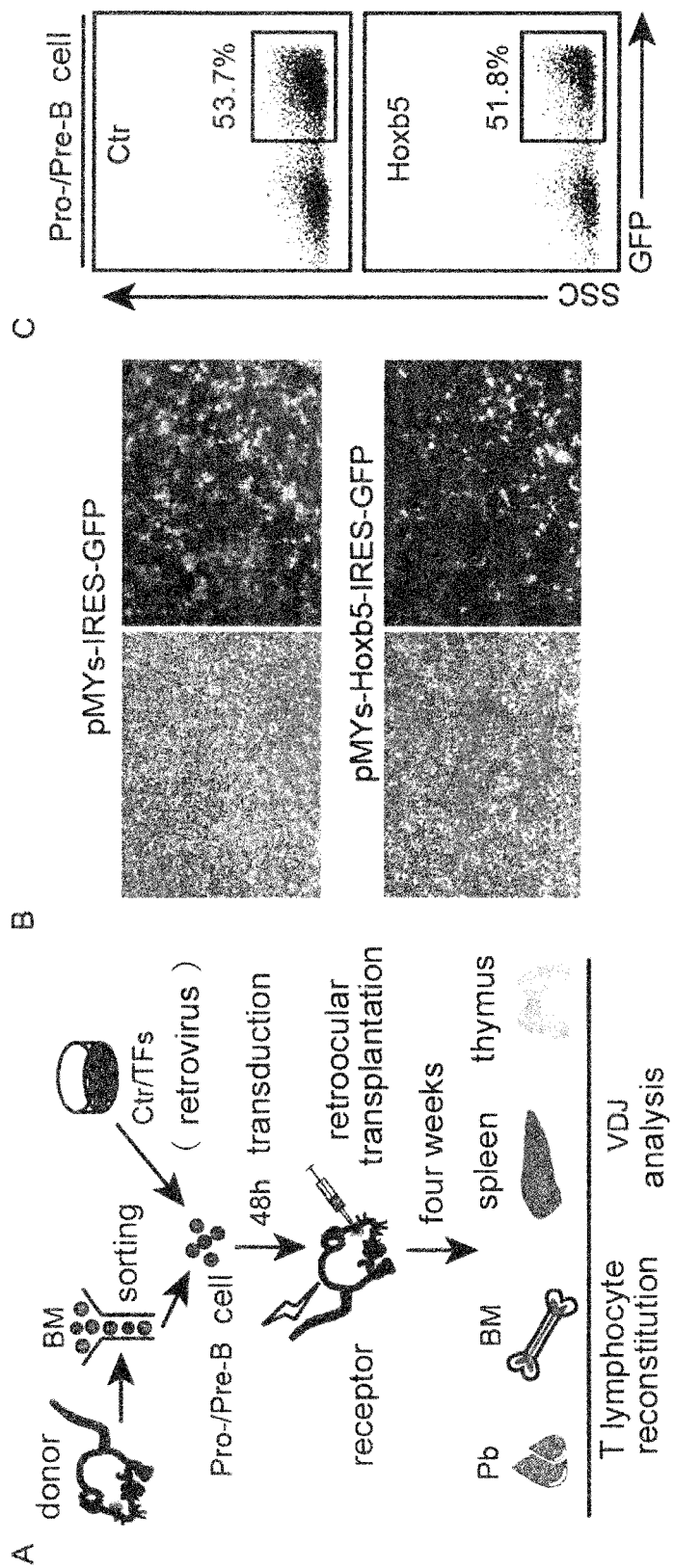
FIG. 1 shows: (A) An experimental design flow chart for the regenerated T cells; (B) Fluorescence EGFP detection showing the efficiency of transfecting Hoxb5 recombinant plasmids into the retroviral packaging plat-E cells of more than 85% (48 hours post-transfection) (C) Flow cytometry analysis showing the transduction efficiency of the Hoxb5 retrovirus infecting Pro-/Pre-B cells of more than 50% (48 hours post-infection).

First, the whole experimental flow chart of the regeneration of T cells through in vivo transdifferentiation of B cells by Hoxb5 was designed (FIG. 1A). Next, the information of restriction enzyme cutting site of Hhob5 gene was analyzed by Lasergene software, XhoI/SnaBI were selected as the upstream and downstream recombination restriction enzyme cutting sites, and the Hoxb5 gene was recombined and constructed into the retroviral vector (pMYs-IRES-EGFP). After the ligated product was transformed by DH5α competence, the positive recombinant clones were screened using an ampicillin plate. DNA sequencing was performed by further combining bacteria solution PCR and extraction of recombinant plasmids to determine the successful recombination of pMY-Hoxb5-IRES-EGFP retroviral plasmids, large scale extraction of which with endotoxin removal was performed for future use. Subsequently, the Hoxb5 recombinant vector was transferred to the retrovirus packaging cell line (Plat-E cells) by calcium phosphate transfection. After 24 hours, the transfection rate was checked with help of a fluorescence microscope to ensure that the transfection rate was ≤85% (FIG. 1B). After 48 hours, the retroviral supernatant containing Hoxb5 was collected for future use. At the same time, 4-6 weeks old mice were sacrificed, and the bone marrow of the mice was removed and prepared into a single cell suspension. Next, the B220+ cells in the bone marrow single cell suspension were enriched by magnetic-bead enrichment method. Pro-/Pre-B cells (CD19$^+$B220$^+$CD93$^+$ IgM$^-$) were sorted out with an ultra-high-speed flow sorter (Moflo Astrios) after being stained with Pro-/Pre-B antibody combination (CD19/B220/CD93/IgM). The sorted Pro-/Pre-B cells were collected after being centrifuged at 500 g at low temperature. Subsequently, the enriched Pro-/Pre-B cells were placed in the B lymphoid cell complete medium to be pre-stimulated and cultured for 12-14 hours. The retrovirus was added to the opti-MEM basal medium at a volume of 1:1, meanwhile 8 μg/ml of polybrene was added and mixed well for future use. Pre-stimulated Pro-/Pre-B cells were collected by centrifugation at 350 g for 5 minutes. Subsequently, the Pro-/Pre-B cells were resuspended using a reconstituted retroviral solution, then placed in a low adhesion 6-well plate and subjected to centrifugal infection at 805 g in a 35° C. constant temperature horizontal centrifuge for 90 minutes. After centrifugation, the 6-well culture plate was placed back to a cell incubator (37° C.; 5% CO$_2$), and allowed to stand and culture for 2 hours. Subsequently, the Pro-/Pre-B cells were collected by centrifugation at 350 g. The Pro-/Pre-B cells were resuspended and cultured with a preheated complete medium to maintain at a density of 2-4 million cells per milliliter. After 24 hours, the centrifugal infection was repeated once. 24 hours after the second infection, a small amount of cells were stained with trypan blue to count and the infection rate of the Pro-/Pre-B cells was analyzed by a flow cytometry. The results showed that the infection rates of both the control group and the Hoxb5 group were more than 50% (FIG. 1C). Subsequently, the suspended cells were collected by centrifugation at 350 g, transplanted at an amount of 6-8 million viable cells per recipient mouse, and the recipient mice were treated with a sub-lethal dose (6.5 Gy) of irradiation for 4 hours in advance. Meanwhile, 1.14 g/L of neomycin sulfate was added to the feeding water of mice to prevent intestinal infection of mice after irradiation.

Figure 2:
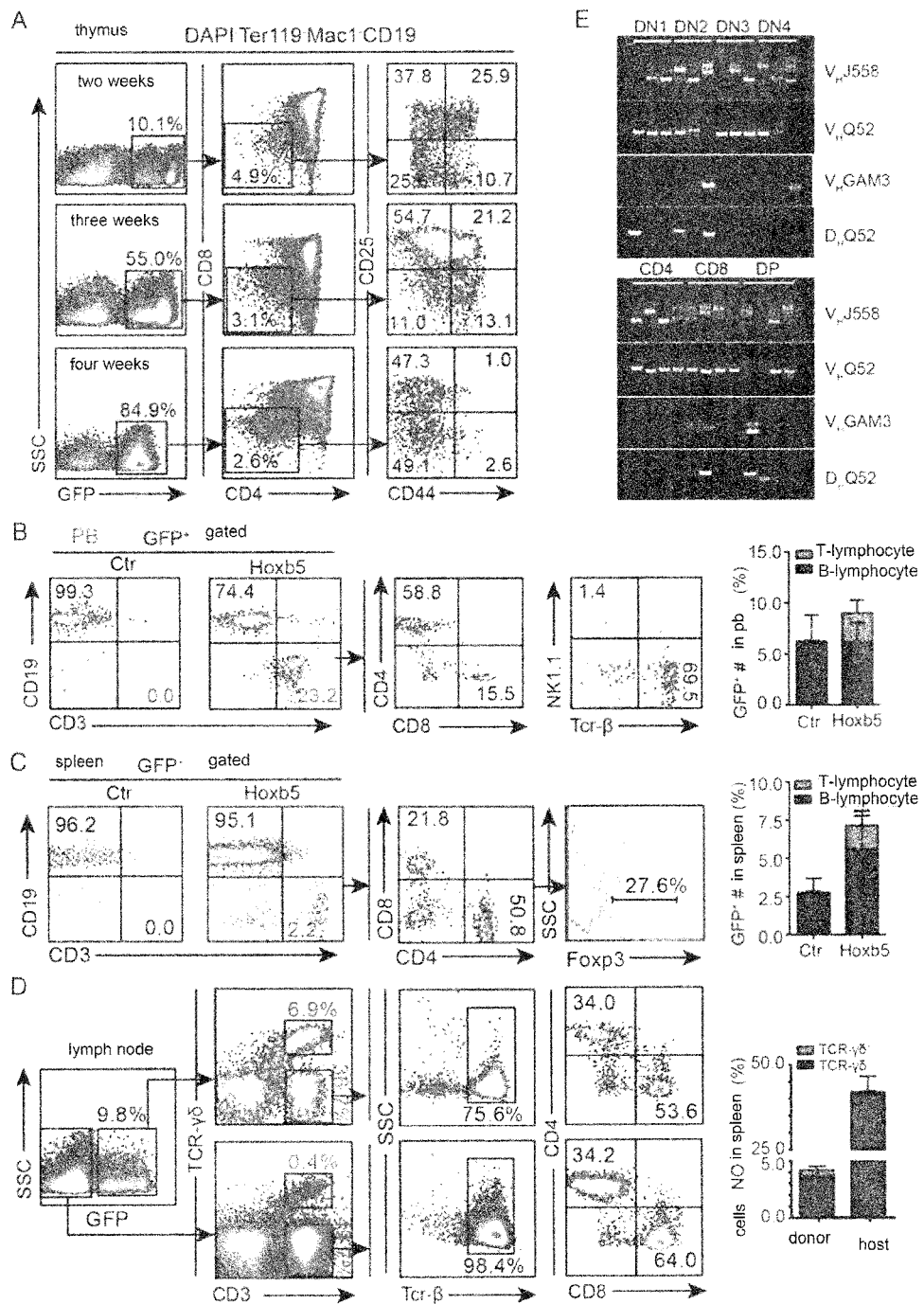
FIG. 2 shows: (A) Flow cytometry analysis of the proportion and composition of the regenerated T cells in the thymus of the recipient mice at 2 to 4 weeks post-transplantation. At the 4th week of transplantation, the composition of donor-derived cells (GFP$^+$) in the peripheral blood (B), spleen (C) and lymph nodes (D) of the recipient mice and classification of the regenerated T cells were analyzed by flow cytometry. Wherein, statistical graphs of three independent repeated experiments were on the right side. (E) PCR detection of B cell-specific VDJ rearrangement of regenerated individual T cells.

2-4 weeks after transplantation, the transplanted recipient mice were sacrificed and analyzed for the generation of T cells in thymus, spleen, lymph nodes, and peripheral blood. The regenerated T lymphocytes were traced with the help of T lymphocyte surface antigen CD3 and endogenous EGFP fluorescent protein. The results showed that only 2 weeks after transplantation, up to 10% of EGFP and CD3 double positive T cells can be found in the thymus of recipient mice: it was confirmed by a further analysis that this population of T cells contained CD4 single positive, CD8 single positive, CD4 CD8 double positive (DP) and CD4 CD8 double negative (DN) T cells (FIG. 2A).

In addition, the DN cells can be classified into four sub-populations in a proportion pattern similar to their physiological state counterpart by a further analysis thereof: DN1 cells ($CD44^+CD25^-$), DN2 cells ($CD44^+CD25^+$), DN3 cells ($CD44^-CD25^+$) and DN4 cells ($CD44^-CD25^-$) (FIG. 2A).

Next, the continuous analysis of the thymocytes of the recipient mice showed that the proportion of the regenerated T cells of $CD3^+EGFP^+$ in the thymuys of the recipient mice was increased gradually over time. At the fourth week of transplantation, more than 80% of thymocytes were the regenerated T cells (FIG. 2A).

In addition, the regenerated T cells in the peripheral blood, spleen and lymph nodes of the recipient mice were analyzed. The results showed that CD4 single positive ancillary T (Th) cells, CD8 single positive cytotoxicity T cells and expression T cell receptor (TCR) beta chain can be detected in the regenerated T cell population in the peripheral blood (FIG. 2B). Regulatory T cells of $Foxp3^+CD4^+$ can be detected in the spleen of the recipient mice (FIG. 2C), while TCR-γδ positive T cells can be detected in the lymph nodes (FIG. 2D).

To further determine whether the regenerated T cells ($CD3^+EGFP^+$) were originated from the Pro-/Pre-B cells, it was identified by analyzing B cell Ig heavy chain VDJ and light chain (κ, δ) rearrangements. PCR detection was performed by flow sorting of single $CD3^+EGFP^+$ cell. Subsequently, the PCR fragment was recovered and ligated to the T vector for sequencing analysis. The results showed that the individual $CD3^+EGFP^+$ fT cells had B cell Ig heavy chain VDJ and light chain (κ, δ) rearrangements, indicating that the T cells were transdifferentiated from B cells (FIG. 2E).

Figure 3:
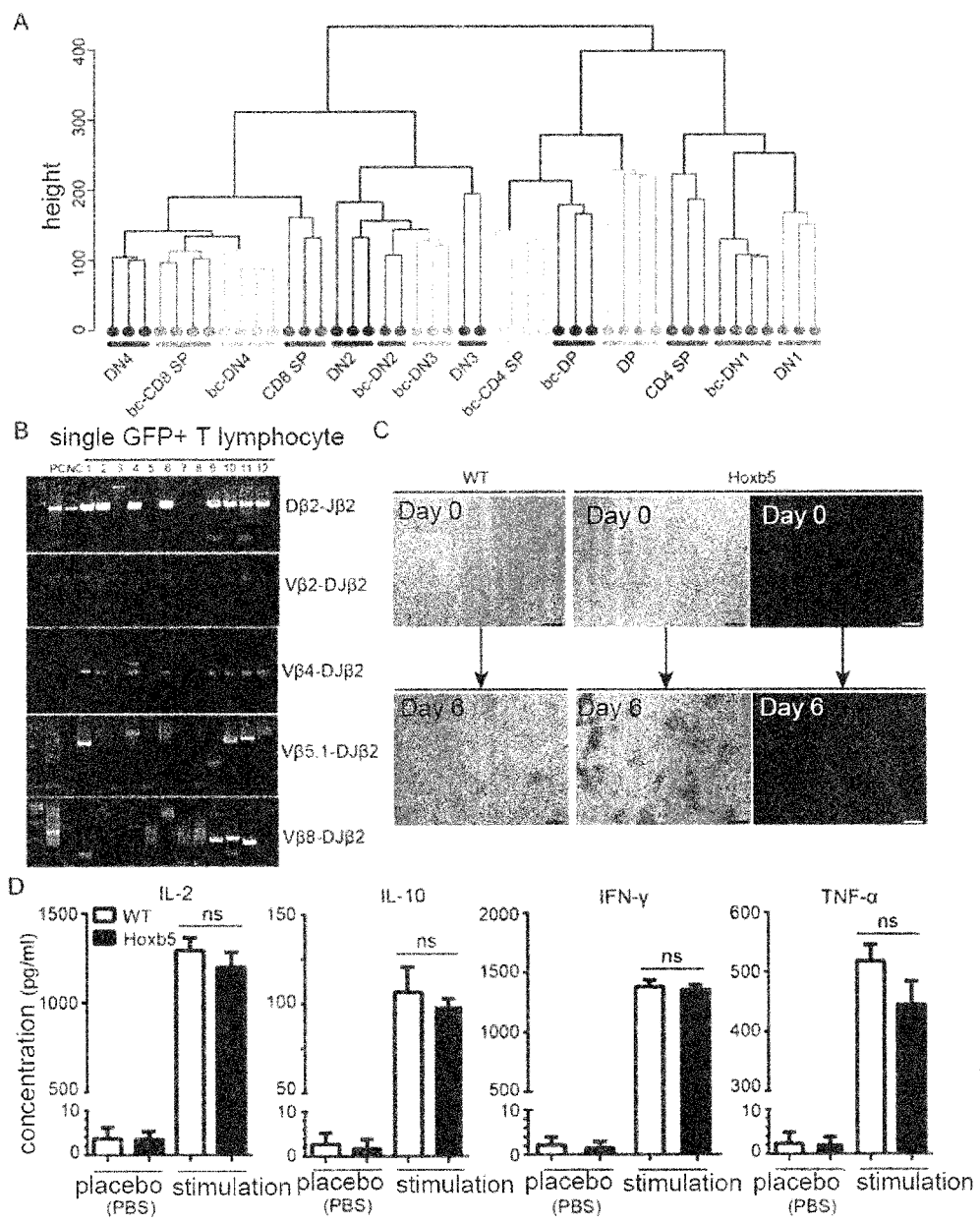
FIG. 3 shows: (A) Cell transcriptomics cluster analysis of various types of regenerated T cells and wild-type T cells in thymus of recipient mice; (B) PCR detection of TCR-β chain rearrangement at different sites in regenerated individual T cell; (C) Representative morphological graph of the proliferation of the regenerated T cells stimulated in vitro by anti-CD3 and anti-CD28 antibodies. Wherein, WT is a wild-type control. (D) ELISA detection of secretion of representative cytokines into the supernatant of the culture medium by regenerated T cells proliferated through in vitro stimulation.

In addition, the inventor has sorted out seven cell populations: DN1, DN2, DN3, DN4, DP, CD4+ single positive, CD8+ single positive cells developed from the regenerated T cells ($EGFP^+$) in the thymus of the recipient mice four weeks post-transplantation to perform the RNA-Seq sequencing analysis. Next, transcriptional expression profiles of the seven populations of cells were analyzed by bioinformatics, and branch cluster analysis was performed. The results showed that the seven populations of regenerated T lymphocytes clustered to their wild type natural counterparts (FIG. 3A). Single mature T cell ($CD4^+/CD8^+$) in the spleen of the recipient mice was sorted further by virtue of flow cytometry to analyze TCR-β rearrangement. Combined with PCR technique and T vector sequencing, the experimental results showed that different regenerated T cells had different TCR-β rearrangements (FIG. 3B). In addition, the inventor has sorted out the mature regenerated T cells in spleen to perform in vitro stimulation proliferation experiment, which were stimulated and cultured for six days in combination with CD3 and CD28 antibodies. The regenerated T cells were able to respond to the stimulation and proliferate in large quantities (FIG. 3C). The supernatant of culture medium was analyzed by ELISA technique, the results showed that a large amount of interleukin-2 (IL-2), interleukin-10 (IL-10), interferon-γ (IFN-γ) and tumor necrosis factor-α (TNF-α) can be secreted by the regenerated T cells proliferated by stimulation. Finally, the health condition of the transplanted recipient mice, especially the T lymphoid hematopoiesis, was continuously tracked. The results showed that the regenerated T cells in the bodies of mice had no risk of tumorigenesis or extremely low risk of tumorigenesis.

Example 2

Figure 4:
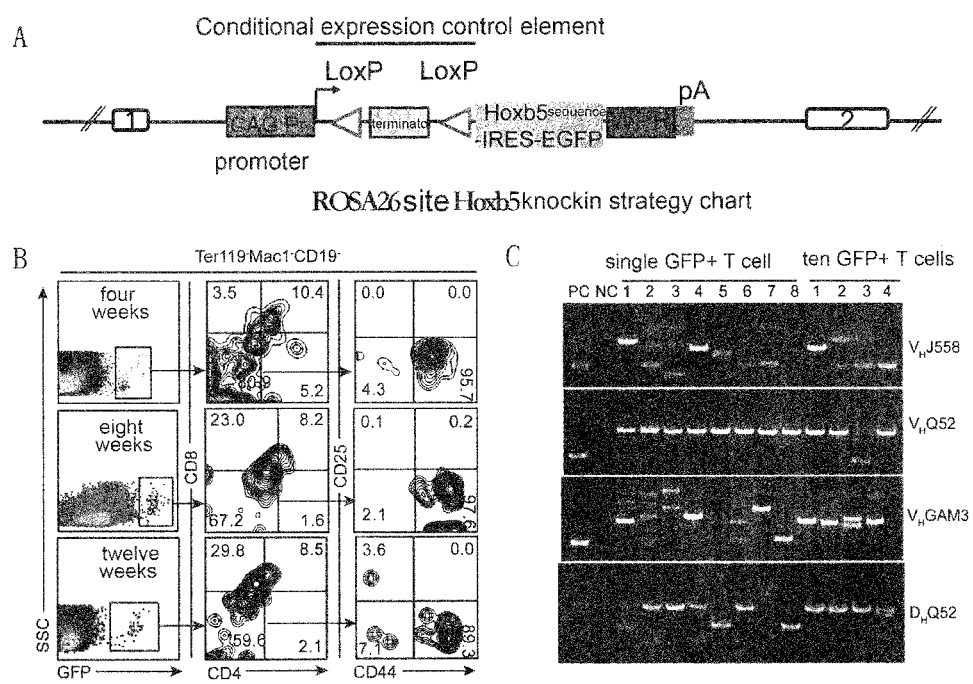
FIG. 4 shows: (A) Construction schematic diagram of Hoxb5 knockin model mice (LSL-Hoxb5) by targeting at ROSA26 locus. (B) Dynamic analysis of proportion and composition of the regenerated T cells (GFP$^+$) in thymus of 4-week-old, 8-week-old, and 12-week-old CD19-Cre LSL-Hoxb5 complex model mice. (C) B cells Ig heavy chain VDJ rearrangement PCR analysis of different heavy chain VDJ rearrangement sites of regenerated individual T cell and ten regenerated T cells ($V_HJ558$, $V_HQ52$, $V_HGAM3$, and $D_HQ52$), which confirmed that the regenerated T cells were derived from B cells.

In order to eliminate potential problems such as uncertainty in the retroviral integration sites and heterogeneity in expression levels, and the like, the inventor has also constructed a Hoxb5 knockin animal model (LSL-Hoxb5) (FIG. 4A). LSL-Hoxb5 CD19-Cre (hereinafter referred to as Hoxb5 mice) was obtained by heterozygosis of Hoxb5 knockin mice with B lymphoid specific expression Cre mode mice CD19-Cre. By analyzing the thymus of Hoxb5 mice, it was found that there were a small amount of regenerated T cells of $CD3^+EGFP^+$ (FIG. 4B). Likewise, the regenerated T cells were sorted out for B cell Ig heavy chain VDJ and light chain (kappa, δ) rearrangements to be identified (FIG. 4C). Combined with T vector sequencing, the results showed that the regenerated T cells had B cell-specific VDJ rearrangements, indicating that they were originated from transdifferentiation of B cells.

Applicant has declared that although the products, methods and uses of the present invention were illustrated by the above examples in the present invention, the present invention is not limited thereto, and it will be apparent to those skilled in the art that any improvements made to the present invention, equivalent replacements and addition of adjuvant ingredients to the products of the present invention, and choices of the specific implementations, etc., all fall within the protection scope and the disclosure scope of the present invention.

The invention claimed is:

1. A method for transdifferentiating B lymphoid cells into functional T cells, comprising:
    (1) introducing a nucleic acid molecule encoding Hoxb5 or a construct comprising the nucleic acid molecule into the B lymphoid cells by transfection or virus infection to obtain transformed B lymphoid cells with overexpressed Hoxb5;
    (2) implanting the transformed B lymphoid cells obtained in step (1) into the body of a subject to induce transdifferentiation to obtain T cell progenitor cells, which then differentiate to obtain functional T cells.

2. The method according to claim 1, wherein the B lymphoid cells comprise pro-B cells or pre-B cells.

3. The method according to claim 1, wherein the nucleic acid molecule encoding Hoxb5 or the construct comprising the nucleic acid molecule further encodes a tracer.

4. The method according to claim 3, wherein the tracer is a fluorescent protein tracer.

5. The method according to claim 4, wherein the fluorescent protein tracer is an EGFP fluorescent protein tracer.

* * * * *